(12) United States Patent
Hughes et al.

(10) Patent No.: US 7,192,610 B2
(45) Date of Patent: Mar. 20, 2007

(54) METHOD OF DEACTIVATING DUST MITE ALLERGENS

(75) Inventors: John Farrell Hughes, Hampshire (GB); Karen Louise Jerrim, Salisbury (GB); Malcolm Tom McKechnie, East Yorkshire (GB)

(73) Assignees: Reckitt Benckiser (UK) Limited, Slough (GB); University of Southampton, Southampton (GB)

( * ) Notice: Subject to any disclaimer, the term of this patent is extended or adjusted under 35 U.S.C. 154(b) by 0 days.

(21) Appl. No.: 10/266,288

(22) Filed: Oct. 7, 2002

(65) Prior Publication Data

US 2003/0086991 A1 May 8, 2003

Related U.S. Application Data

(63) Continuation of application No. PCT/GB01/01572, filed on Apr. 9, 2001.

(30) Foreign Application Priority Data

Apr. 7, 2000 (GB) ................... 0008633.0
Oct. 2, 2000 (GB) ................... 0024018.4

(51) Int. Cl.
*A61K 36/00* (2006.01)
*A61K 36/13* (2006.01)
*A01N 25/00* (2006.01)

(52) U.S. Cl. .............. 424/725; 424/769; 424/770; 424/405

(58) Field of Classification Search ............. 424/725, 424/195.1, 736, 770, 773
See application file for complete search history.

(56) References Cited

U.S. PATENT DOCUMENTS

| | | | |
|---|---|---|---|
| 4,806,526 A | 2/1989 | Green | |
| 5,186,722 A * | 2/1993 | Cantrell et al. | ............... 44/605 |
| 5,189,987 A * | 3/1993 | Stanislowski et al. | ...... 119/171 |
| 5,271,947 A | 12/1993 | Miller et al. | |
| 5,399,282 A * | 3/1995 | Hansen et al. | ............... 510/400 |
| 5,885,600 A * | 3/1999 | Blum et al. | ................. 424/405 |
| 6,086,853 A | 7/2000 | Michaels | |
| 6,087,402 A | 7/2000 | Zocchi et al. | |
| 6,130,253 A * | 10/2000 | Franklin et al. | ............. 514/690 |
| 6,147,091 A * | 11/2000 | Kruger et al. | .............. 514/315 |
| 6,294,576 B1 * | 9/2001 | Mori | ......................... 514/531 |
| 6,500,445 B1 * | 12/2002 | Pullen | ......................... 424/405 |
| 6,663,860 B1 * | 12/2003 | Tvedten | ................... 424/94.63 |
| 2002/0022043 A1 * | 2/2002 | Miller | ......................... 424/403 |
| 2004/0127553 A1 * | 7/2004 | Hallahan | ..................... 514/456 |

FOREIGN PATENT DOCUMENTS

| | | |
|---|---|---|
| GB | 2 327 596 A | 2/1999 |
| GB | 2 329 587 A | 3/1999 |
| GB | 2 329 588 A | 3/1999 |
| GB | 2329587 * | 3/1999 |
| JP | 10201836 A | 8/1998 |
| JP | 2000095604 * | 4/2000 |
| WO | WO 93/15774 | 8/1993 |
| WO | WO 97/10475 A1 | 3/1997 |
| WO | WO 99/08722 A1 | 2/1999 |
| WO | WO 99/15208 A1 | 4/1999 |
| WO | WO 00/01429 A1 | 1/2000 |
| WO | WO 00/38512 | 7/2000 |

OTHER PUBLICATIONS

Rosencrans, J.: Dining to the Sound of Roaring Mowers; Cincinnati Post, Cincinnati, Ohio (Jul. 1997), pp. 1-2.*
Lawless, J. :Essential Oils; Element Books, Inc., Boston, MA (1995) p. 134.*
Brody, J. Ragweed Going, But Dust Mites a Year-Round Plague; Houston Crhonical Sep. 30, 1990, p. 14, pp. 1-3 of web page print-out from ProQuest.*
Hurley, J. Household Pests; Toronto Star, Nov. 17, 1996, p. B8, pp. 1-5 of web page print-out from ProQuest.*
Shepard, L. Something to Sneeze at: Home Hides Hazards for Allergy Sufferers: Milwaukee Journal Sentinel, Jan. 5, 1997, p. 10, pp. 1-2 of web page print-out from ProQuest.*
Trausch, S. A Mite-Y Big Problem; Boston Globe Oct. 24, 1990, p. 19, pp. 1-3 of web page print-out from ProQuest.*
The Tea Tree Oil Encyclopedia. 1996. Karedon Publishing Co. United Kingdom. p. 129.*

* cited by examiner

*Primary Examiner*—Christopher R. Tate
(74) *Attorney, Agent, or Firm*—Fish & Richardson P.C.

(57) ABSTRACT

A method is provided for deactivating a Der-p and/or Der-f allergen which comprises volatilizing into a space to be treated a deactivating amount of a volatile oil selected from cajeput oil (tea tree oil) or an oil comprising one or more terpene hydrocarbons.

8 Claims, 6 Drawing Sheets

METHOD OF DEACTIVATING DUST MITE ALLERGENS

CROSS-REFERENCE TO RELATED APPLICATIONS

Figure 1:
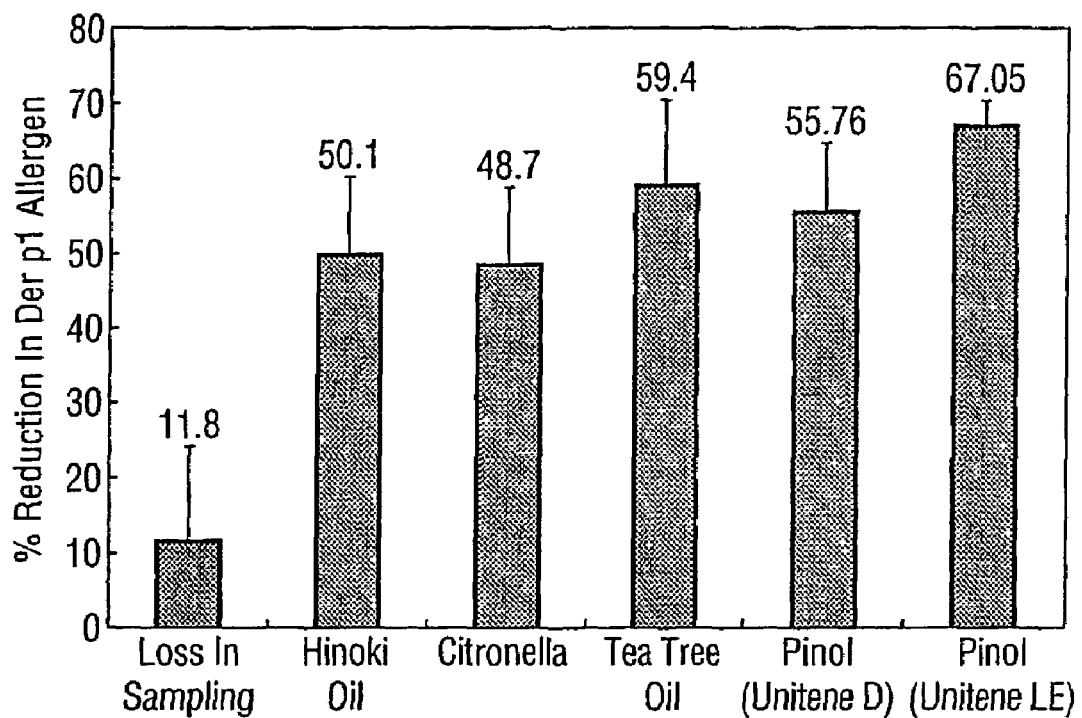

This application is a Continuation of International Application No. PCT/GB01/01572, filed Apr. 9, 2001, which was published in the English language on Oct. 18, 2001, under International Publication No. WO 01/76371 A1 and the disclosure of which is incorporated herein by reference.

BACKGROUND OF THE INVENTION

The present invention relates to a method of deactivating dust mite allergens.

Various allergens are known which are transported through the air to trigger a human reaction. For example, it has been known for a long time that house dust can trigger allergenic reactions in humans, such as asthma and rhinitis. It was reported as early as 1928 that it was the dust mites in the dust that were the primary source of the allergenic response, but it was only in the 1960's that researchers appreciated their significance.

It is believed that the feces of the house dust mite, Dermatophogoides farinae (known as Der-f) and Dermatophagoides pteronyssinus (known as Der-p), trigger the immune response of the body, thereby giving rise to well known allergenic symptoms. A review of this is given in *Experimental and Applied Acarology*, 10:167–186 (1991).

One way to overcome these allergenic responses has been to vacuum clean surfaces, such as carpets, that contain the dust mites and their feces thoroughly and often, but that is both time consuming (it has to be regularly done to ensure an allergenic free environment) and is very dependant on the efficiency of the vacuum cleaner and filter bag used, e.g., micron filter bags or two layer vacuum bags.

An alternative method of creating an allergen-free environment has been to denature the allergen, for example, by using an allergen denaturant applied to airborne allergens by means of an aerosol spray device. Such a device produces an aerosol spray when activated and this spray may be targeted at any space which is to be treated.

The allergens to be treated are airborne particles and the use of a known aerosol spray device results in a low collision rate between the allergen denaturant and the airborne allergens. The practical consequence of such a low collision rate is that the allergen denaturant must be used in a high amount in order to be effective. There may be other consequences such as, in the case where the aerosol spray composition includes a perfume or fragrance, a strong perfume smell or a limited fragrance choice.

PCT/GB98/02863 describes a method for deactivating allergens derived from the Der-f and/or Der-p dust mite species, which comprises contacting the allergen with a deactivating amount of one or more of a variety of 28 deactivants as described. The deactivants which are specified for use include cedarwood oil, hinoki oil and thymol (6-isopropyl-m-cresol).

BRIEF SUMMARY OF THE INVENTION

A method of deactivating at least one of a Der-p and a Der-f allergen is provided. The method comprises volatilizing into a space to be treated a deactivating amount of a volatile oil by heating the volatile oil to volatilize the oil, or by volatilizing the volatile oil from an ultra-sonic jet nebulizer, wherein the volatile oil is selected from the group consisting of cajeput oil (tea tree oil) and an oil comprising at least one terpene hydrocarbon.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 1 is a graphical representation of the test results from Example 1 below;

FIG. 2 is a graphical representation of the test results from Example 2 below;

FIG. 3 is a graphical representation of the test results from Example 3 below;

FIG. 4 is a graphical representation of the test results from Example 4 below;

FIGS. 5 and 6 are graphical representations of the test results from Example 5 below;

FIG. 7 is a graphical representation of the test results from Example 6 below;

FIG. 8 is a graphical representation of the test results from Example 7 below;

FIG. 9 is a graphical representation of the test results from Example 8 below;

FIG. 10 is a graphical representation of the test results from Example 9 below; and FIG. 11 is a graphical representation of the test results from Example 10 below.

DETAILED DESCRIPTION OF THE INVENTION

We have now discovered a group of novel allergen denaturants for the house dust mite Der-p allergen which are derived from natural oils and which can be delivered as a vapor to deactivate the allergens. Accordingly, the present invention provides a method of deactivating a Der-p and/or Der-f allergen which comprises volatilizing into a space to be treated a deactivating amount of a volatile oil selected from cajeput oil (tea tree oil) or an oil comprising one or more terpene hydrocarbons.

Suitable oils comprising one or more terpene hydrocarbons which may be used in the present invention are those which are generically referred to as pinol, such as these sold under the names Unitene® D and Unitene® LE (Bush Boake Allen). The main component of both Unitene® D and Unitene® LE comprises limonene as its major constituent. Unitene® D contains significant quantifies of cineole and terpinolene, while Unitene® LE contains significant quantities of terpene alcohols.

Cajeput oil, which is generally known as tea tree oil, is obtained from the Melaleuca leucandra, Melaleuca quinquenervia, or other Melaleuca species. The main components of tea tree oil are cineole and terpinene-4-ol.

There are various methods which can be used to volatilize the volatile oils into the air, and these delivery methods are discussed below.

The volatile oil may be volatilized by the use of heat to vaporize the oil. For example, the volatile oil may be floated on water in an oil burner or heated directly in an oil burner.

Alternatively, the volatile oil may be vaporized from a heated wick dipped into a reservoir of the volatile oil.

Another method of volatilizing the volatile oil is from an ultra-sonic jet nebulizer, which contains water with the volatile oil floated on the surface of the water.

A further method of volatilizing the volatile oil is by the ventilation of a source of the volatile oil using an ion wind. An ion wind generates an ionized air flow which facilitates the evaporation and dispersal of the volatile oil into the air. A unipolar charge is transferred to the molecules of the oil which is evaporated. Optionally, the source of the volatile oil may be heated in order to assist evaporation. The ion wind not only facilitates the evaporation and dispersal of the volatile oil, but also has the added advantage that the ion wind generating device has no moving parts and thus operates at very low noise levels. The ion wind thus acts as an essentially silent fan. The charged molecules of the vaporized oil are attracted to particles in the air with an opposite or neutral charge, and so may be more efficient at denaturing airborne allergens than uncharged molecules. The charged molecules are also attracted to surfaces in the environment which are being treated, and thus allergens on surfaces are also treated.

A method and apparatus for dispersing a volatile composition, such as a volatile oil, is described in our PCT Application No. PCT/GB99/04312.

It will be understood that in order to obtain the desired level of the volatile oil evaporated into a room, the rate of evaporation of the oil, the surface area across which the volatile oil is evaporated, and the ion wind speed will need to be taken into account. Higher ion wind speeds will provide faster evaporation of the volatile components, and thus the surface area across which the volatile oil is evaporated will need to be adapted to the air flow speed.

The benefit of charging the molecules of the volatile oil using an ion wind is two-fold. The individual molecules are attracted as the allergen particles and, since all of the molecules have the same polarity charge, they are repelled one from another. Accordingly, the molecules tend to spread out to a great extent as compared to uncharged molecules.

Allergen particles are normally electrically isolated from their surroundings and will typically be at a potential which is the same as that of their surroundings. An isolated allergenic particle within a cloud of electrically charged molecules is likely to cause distortion of the electrical field so that the attraction of the charged molecules onto the allergen particle will be enhanced.

The volatile oil may be used as such, or may be presented in the form of an emulsion. Generally, the emulsion will be an oil-in-water emulsion comprising up to about 5% by weight of the oil. The formation of emulsions is generally well known in the art and is described, for example, in *Modern Aspects of Emulsion Science*, edited by Bernard P. Binks, The Royal Society of Chemistry (1998) and *Surfactant Science and Technology*, Second Edition, Drew Myers, VCH Publishers, Inc (1992).

In a still further aspect of the present invention, the volatile oil is incorporated into a candle which is burnt in the space to be treated. In carrying out this aspect of the present invention, the candle which is burnt will generally comprise at least about 2% by weight of the volatile oil, preferably at least about 5% by weight of the volatile oil, and more preferably at least about 10% by weight of the volatile oil.

By the term "candle" as used herein is meant a solid, semi-solid or gelled body of a combustible material which contains an axially embedded combustible fibrous wick. When the wick of a candle is lit, the heat so generated melts the combustible material, and the resulting liquid flows up the wick by capillary action and is combusted.

Typically, the combustible body of the candle may be a blend of organic materials, such as beeswax, paraffin wax, montan wax, carnauba wax, microcrystalline wax, fatty alcohols, fatty acids, fatty esters and/or natural and synthetic resins. Clear candles may comprise as the combustible material a gel comprising mineral oil containing blends of diblock and triblock copolymers based on synthetic thermoplastic rubbers, or a gel obtained by combining a liquid base material of a hydrogenated polyolefin, a gelling agent, and optionally a gel enhancing agent.

A wick normally extends longitudinally through the candle body. More than one wick may be used, if desired, but usually a single wick is centrally disposed in the candle body. When a candle wick is ignited, the wick is adapted to burn gradually so that both the wick and the candle body are consumed.

Typically, the weight of candle which is burnt in a particular space to be treated will depend upon the actual volume of the space, e.g., room, to be treated. An appropriate allergen denaturing effect can be obtained in accordance with the method of the invention by burning in a room having a volume of about 25 to 30 $m^3$ a candle weighing approximately 150 g before testing containing about 5% by weight of the volatile oil for a period of about five hours. The amount of the volatile oil which is released from the burning candle can be calculated by weighing the candle at about one hour intervals.

The length of time for which the candle is burnt in the space to be treated will generally be for up to about two hours, generally up to about five hours, although in some circumstances the candle may be burnt for a longer period of time, such as about ten hours or more. However, it will be understood by those skilled in the art that an allergen denaturing effect will be obtained even if the candles containing the selected volatile oils are burnt for a lesser period of time.

The volatile oil may also be delivered by means of a nebulizer in which oil is floated on the surface of water in the nebulizer, or is provided as an oil-in-water emulsion in the nebulizer. The nebulizer comprises a piezo-ceramic element which vibrates in the liquid (at 2–5 MHz) and a plume of liquid is generated by ultrasonic streaming. A dense cloud of very small droplets (less than about 5 μm) is then expelled from the surface of the liquid. A fan may be used to assist the expulsion of the nebulized droplets from the vessel.

The present invention will be further described with reference to the following specific, non-limiting Examples.

Control Pre-treatment Allergen Level

When using house dust for allergen denaturing tests, an inherent difficulty is the variability of the amount of allergen in each small sample, even when taken from the same dust reservoir. The amount of dust in the pre-treatment sample must be accurately estimated in order to determine the extent of any allergen denaturing. In these tests, the dust sample was applied to the test exposure surface and then one half of this surface dust was removed to measure the control pre-treatment allergen level of that specific sample. Each control was directly relevant to each sample, which gave the best possible estimate of the level of allergen in the sample before exposure to possible denaturant.

Unless specified, the following Examples all measure the reduction of the house dust mite (Dermatophagoides pteronyssinus) allergen (Der-p1).

EXAMPLE 1

House dust was passed through a number of sieves and the fraction smaller than 53 μm was collected. 0.1 g of dust was placed in a small sieve to distribute it evenly over the test surface, an aluminum tray 0.6 m×1 m. The dust was applied to the tray by moving the sieve continuously over the surface. As a pre-treatment control, one half of the dust was then removed by suction onto an inline filter and the weight was recorded. The tray was then placed in a plastic lined booth measuring 0.8 m×0.8 m×1.5 m. An oil burner containing 800 μl of the test sample floated on 6 ml of distilled water was placed in the booth, and the booth was sealed. The oil burner candle was lit and allowed to burn until all the liquid had been vaporized (approx. 1 hour). The candle was then smothered and the dust was left exposed in the booth. After 24 hours, the tray was removed, the dust was collected from it, and its weight was recorded. The booth was washed with strong detergent between tests of the same chemical and the booth lining was changed between test chemicals.

The test samples evaluated were:
Hinoki Oil (comparative)
Citronella Oil (comparative)
Tea Tree Oil
Pinol (Unitene® D)
Pinol (Unitene® LE)

The test samples were assayed for Der-p1 using an ELISA (Enzyme Linked Immunosorbent Assay) to determine the allergen content, which was then related to the weight of dust that had been present in each sample. All of the samples were normalized to compare the amount of allergen expected to be present in a 0.1 g sample of dust. The percentage differences between the control sample and the exposed samples were then obtained and are presented in FIG. 1.

The differences in the amounts of allergen reduction after exposure to any of the volatile oils released from the oil burner when compared to the inherent loss in sampling were significant when compared in a two-tailed t-test. Therefore, in conditions of the test, exposure to the above oils released from an oil burner resulted in a significant reduction in the allergen contained in the dust samples.

EXAMPLE 2

House dust was passed through a number of sieves and the fraction smaller than 53 μm was collected. 0.1 g of dust was placed in a small sieve to distribute it evenly over the test surface, an aluminum tray 0.6 m×1 m. The dust was applied to the tray by moving the sieve continuously over the surface. As the pre-treatment test control, one half of the dust was then removed by suction onto an in-line filter and the weight was recorded. The tray was then placed in a plastic lined booth 0.8 m×0.8 m×1.5 m.

For control tests, dust was distributed on the tray, the pre-treatment control was collected, and the dust was left in the booth for 24 hours. The tray was then removed and the dust was collected from the tray and weighed. In subsequent tests, 800 μl of volatile oil was added to 150 ml of distilled water in a nebulizer. The tests were then completed as in the control tests. The booth was washed with strong detergent between tests.

The samples evaluated were:
Tea Tree Oil
Pinol (Unitene® D)
Pinol (Unitene® LE)

Figure 2:
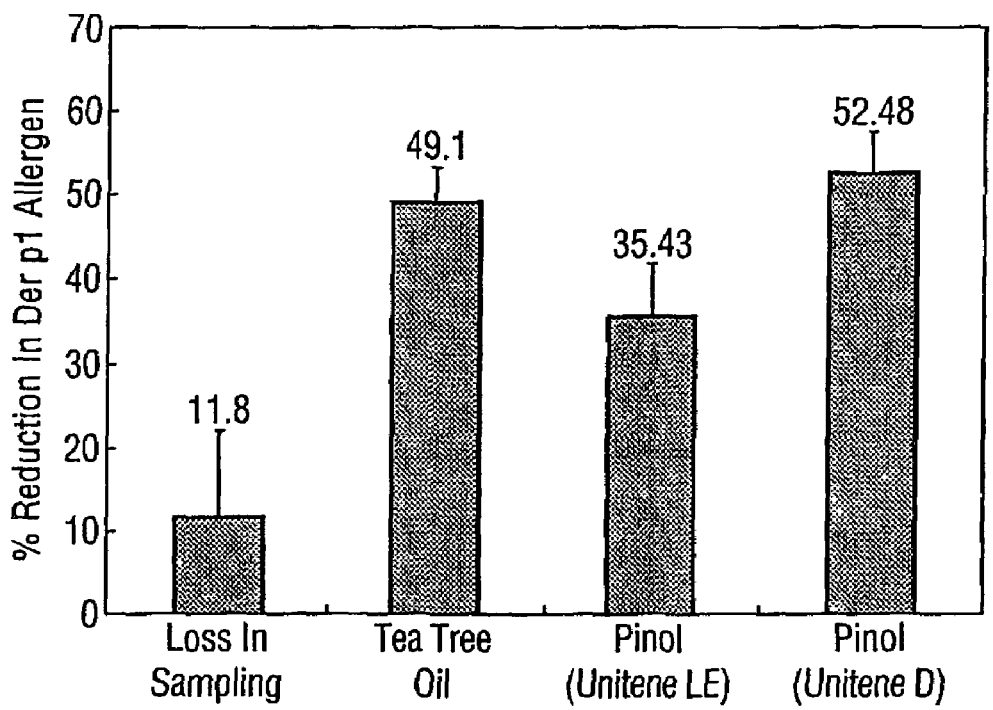

The collected dust samples were assayed for Der-p1 using an ELISA to determine the allergen contents, which were then related to the weight of dust that had been present in each sample. All of the samples were normalized to compare the amount of allergen expected to be present in a 0.1 g sample of dust. The percentage differences between the control sample and the exposed samples were then obtained and are presented in FIG. 2.

The differences in the amounts of allergen reduction after exposure either to tea tree oil or Unitene® D released from the nebulizer, when compared to the loss in sampling control, were significant ($P<0.05$) when compared on a two tailed t-test. Therefore, in the conditions of the test, exposure to either tea tree oil or Unitene® D released from a nebulizer resulted in a significant reduction in the allergen contained in the dust samples.

EXAMPLE 3

Dust was collected from vacuum cleaner bags and passed through a series of sieves down to 53 microns. Clean petri dishes were labeled with the chemical to be tested and lined with filter paper. 0.3 g of dust was added to each dish and spread evenly over the filter paper. 0.1 g of dust was then removed from the filter paper for a control sample. The remaining dust was then redistributed evenly over the filter paper. 2.4 g±0.2 g of test chemical was sprayed onto the dust sample. The dust sample was left open to the air until the filter paper was dry. The dust was collected into eppendorfs and the weight of dust recovered was measured. 1 ml of 1% Bovine Serum Albumin-Phosphate Buffered Saline-Tween (BSA-PBS-T) was added to the control samples. 1 ml of 5% BSA-PBS-T was added to the test samples. The samples were left overnight in the refrigerator and then centrifuged for 5 minutes at 13,000 rpm. The supernatant was pipetted into an eppendorf for assay by Der-p1 ELISA.

Figure 3:
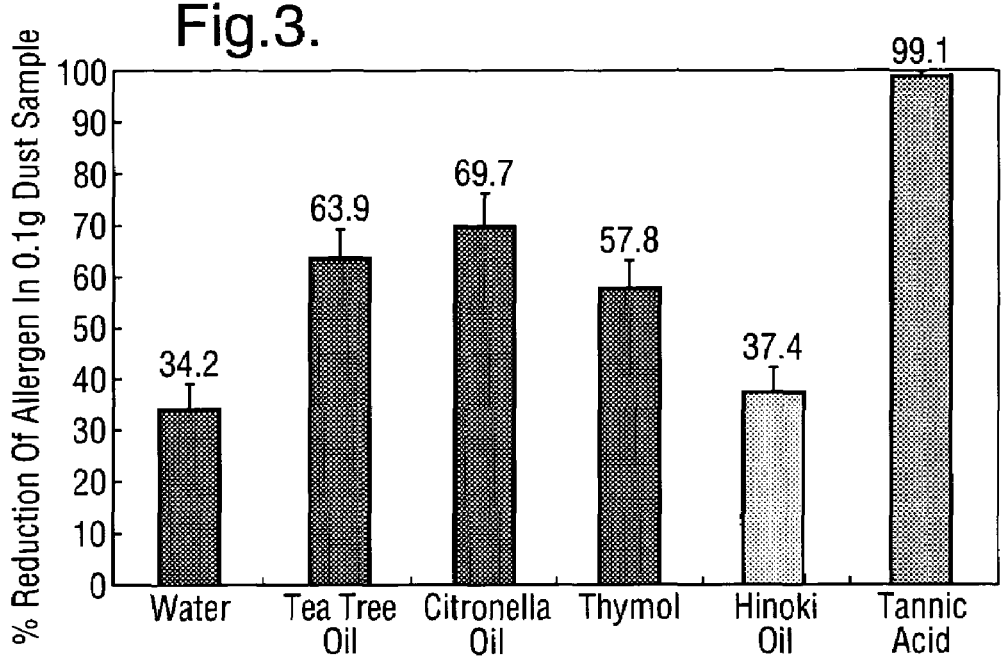

The test liquids were:
Distilled water
2% Tea Tree Oil in distilled water (plus 0.1% Tween)
2% Citronella Oil in distilled water (plus 0.10% Tween)
1% Thymol in distilled water (plus 0.8% Tween)
2% Hinoki Oil in distilled water (plus 0.1% Tween)
2% Tannic Acid Five replicates were completed for each test liquid. The allergen content of the control for each replicate was compared with the test sample allergen. The percentage reductions in allergen between the control and the test were determined for each replicate. The average allergen reductions of all five replicates are presented in FIG. 3.

The water tests showed an average allergen reduction of 34.2%. The addition of Tea Tree Oil to the dust reduced the allergen by another 29.6%. This difference was significant when compared on a t-test ($t=4.08$). Thymol reduced the allergen by 23.6% more than the water alone tests, which difference was significant when compared on a t-test ($t=3.3$). Finally, the addition of tannic acid to the dust reduced the allergen by an average of 99.15% in the tests.

When taking the reduction of allergen in the water samples into account, some of the test liquids still significantly reduced the allergen content in the dust samples. Tannic acid was used as a positive control, as it is known to denature allergen, and its effect was recorded in the tests. Tea tree oil significantly reduced the allergen content in the dust samples.

EXAMPLE 4

Method

The tests were completed in 28 m³ test rooms with no windows and a door that was closed throughout the duration of the test. The rooms did not contain any furniture and had easily cleaned floors of non-reactive resin. Six test areas 0.7 m×0.7 m were marked out on the floor of each room with tape. Each test area was divided into two halves. Test dust had been obtained from household vacuum cleaner bags. House dust was passed through a number of sieves and the fraction smaller than 53 microns was collected. 0.1 g of dust was placed in a small sieve to distribute it evenly over the test surface. The dust was applied by moving the sieve continuously over the surface. Dust was removed from half of each of the six test areas by suction of 20 l/min through an in-line glass fiber filter (2.5 cm diameter) and the weight recorded as the pre-treatment controls. The selected test candles weighing approximately 150 g before testing were lit and placed in the rooms for five hours. The candles were then smothered, and the dust was left exposed in the rooms for sixteen hours. The dust was then collected as for the controls and weighed.

The collected samples were assayed by Der-p1 ELISA to determine the allergen contents, which were then related to the weight of dust that had been present in each sample. All the samples were normalized to compare the amount of allergen expected to be present in a 0.1 g sample of dust. The percentage differences between the control samples and the exposed samples were then obtained and are presented in FIG. 4.

During the five hour burn period, approximately 27 g of each of the candles was burnt. For candles B and C detailed below, this equated to a release rate of 270 μl of essential oil per hour.

Tests completed were:

Test Description
  A. Unfragranced candle, room relative humidity (rh)
  B. 5% w/w Tea Tree oil candle, room rh
  C. 5% w/w Unitene LE candle, room rh
  M. No Treatment, room rh
  The room rh recorded during the tests was between 50 and 57%.

Results

Figure 4:
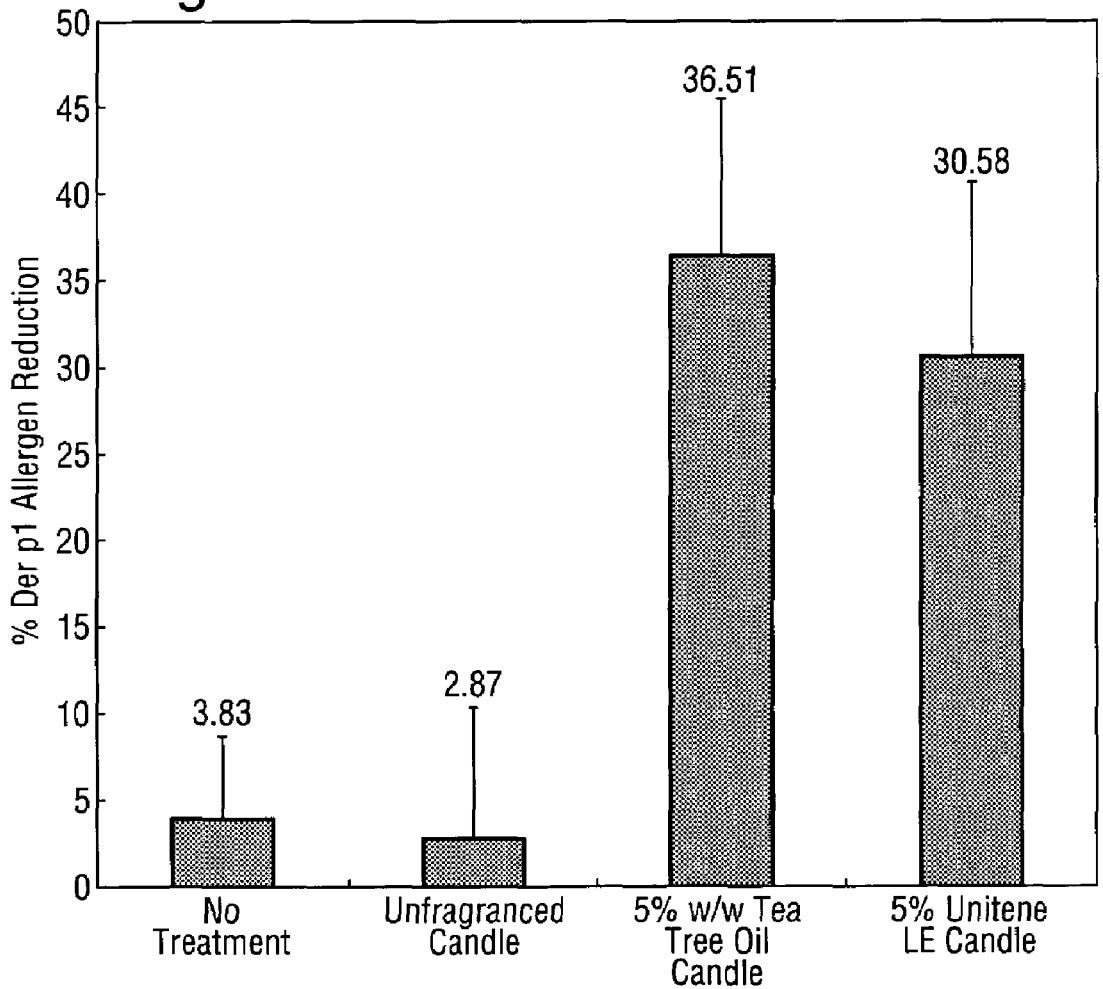

It can be seen from FIG. 4 that there is a significant reduction (P<0.05) Der-p1 allergen content of dust exposed to both the tea tree oil (36.5%) and Unitene® LE (30.6%) candle as compared to the no treatment control (t=3.19 and 2.38 respectively).

Discussion

The results indicate that a significant reduction in allergen can be achieved in a room environment by burning candles containing either tea tree oil or Unitene® LE for five hours.

EXAMPLE 5

Method

British (containing Der-p1) or American (containing Der-f1) house dust was passed through a number of sieves and the fraction smaller than 53 microns was collected. 0.1 g of dust of the selected origin was placed in a small sieve and distributed evenly over the test surface, an aluminum tray 0.6 m×1 m, which could be easily cleaned with strong detergent. The dust was applied to the tray by moving the sieve continuously over the surface. Half of the dust was then removed by suction of 20 L/min through an in-line glass fiber filter (2.5 cm diameter) and the weight recorded as the pre-treatment control. The tray was then placed in a plastic booth 1 m×0.7 m×0.7 m.

The candle to be tested weighing approximately 150 g was placed in the booth. The candle was lit and the booth door closed. After approximately two hours, the temperature and humidity in the booth were measured. The candle was allowed to burn for a total of five hours and was then smothered and the dust left exposed in the booth for 17 hours. The tray was then removed and the booth ventilated. The dust was vacuumed from the tray onto a filter and weighed.

Test candles evaluated were:
  Control candle
  5% Tea Tree Oil candle
  5% Pinol (Unitene® LE) candle Six single exposure replicates were completed for each candle. The collected samples were assayed by Der-p1 or Der-f1 ELISA to determine the allergen contents, which were then related to the weight of dust that had been present in each sample. All the samples were normalized to compare the amount of allergen expected to be present in a 0.1 g sample of dust. The percentage differences between the control sample and the exposed samples were then obtained.

Figure 5:
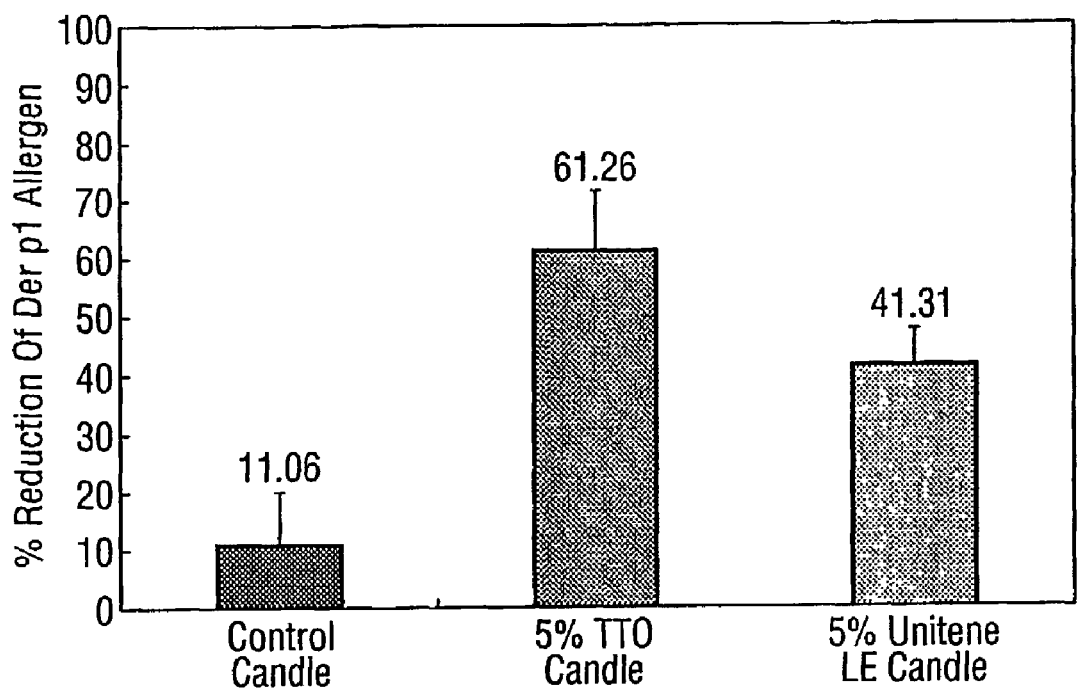
Figure 6:
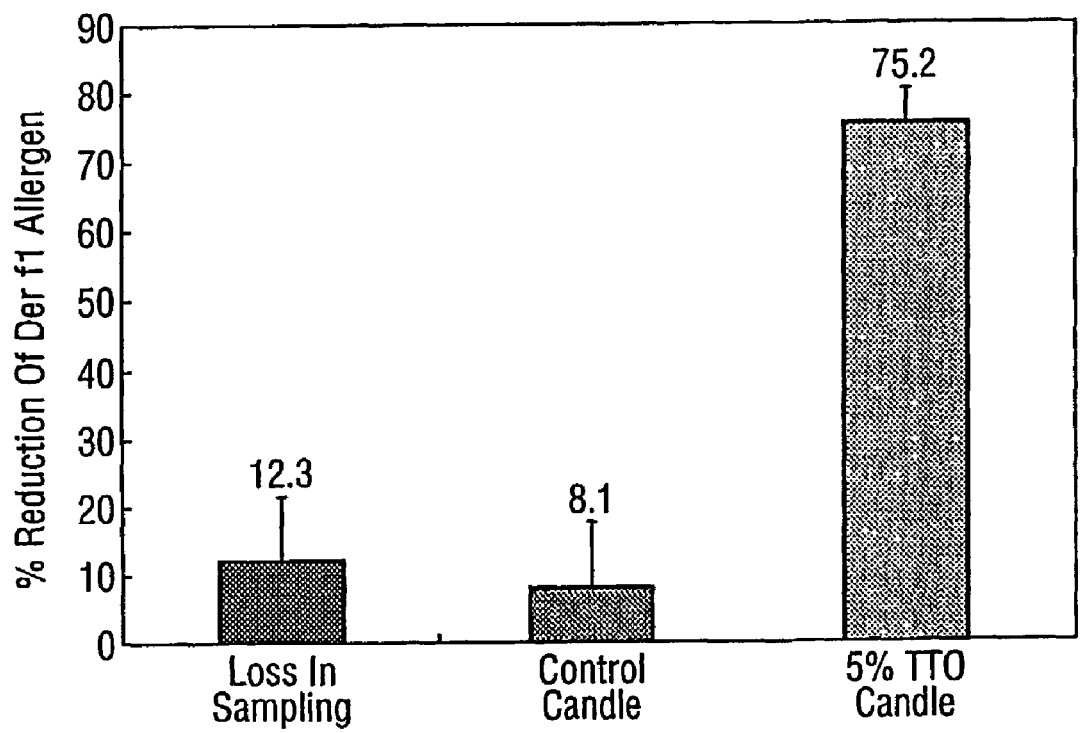

The results for Der-p1 are presented in FIG. 5 and the results for Der-f1 are presented in FIG. 6.

The reduction of Der-p1 allergen concentration in the dust was significant after exposure to either the tea tree oil or Unitene® LE candles, and the reduction in Der-f1 allergen concentration in the dust was significant after exposure to the tea tree oil candle.

EXAMPLE 6

The general procedure of Example 5 was repeated but with three repeated exposures to a candle containing 5% tea tree oil burnt for five hours (i.e., total 15 hours burn), as compared to a single exposure to a candle containing 5% tea tree oil burnt for 5 hours or to a control candle. Six replicate experiments were completed.

Figure 7:
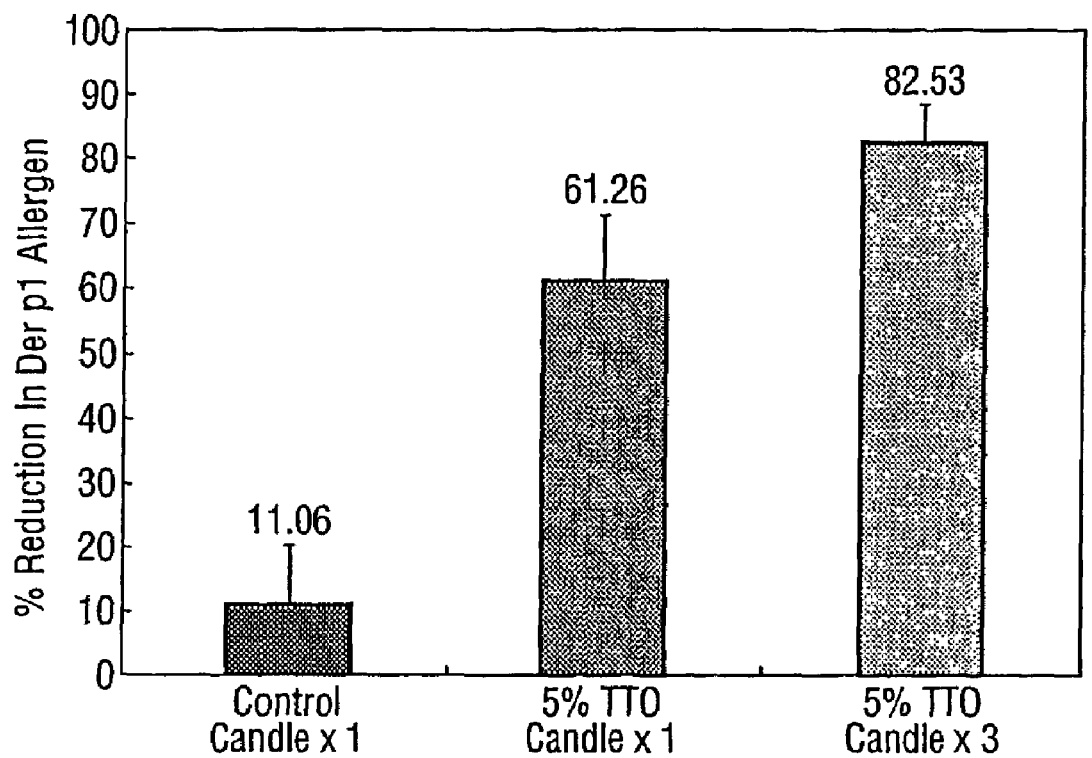

The results are given in FIG. 7. It will be noted that repeated exposure further reduced the Der-p1 allergen concentration of dust on a surface.

EXAMPLE 7

Figure 8:
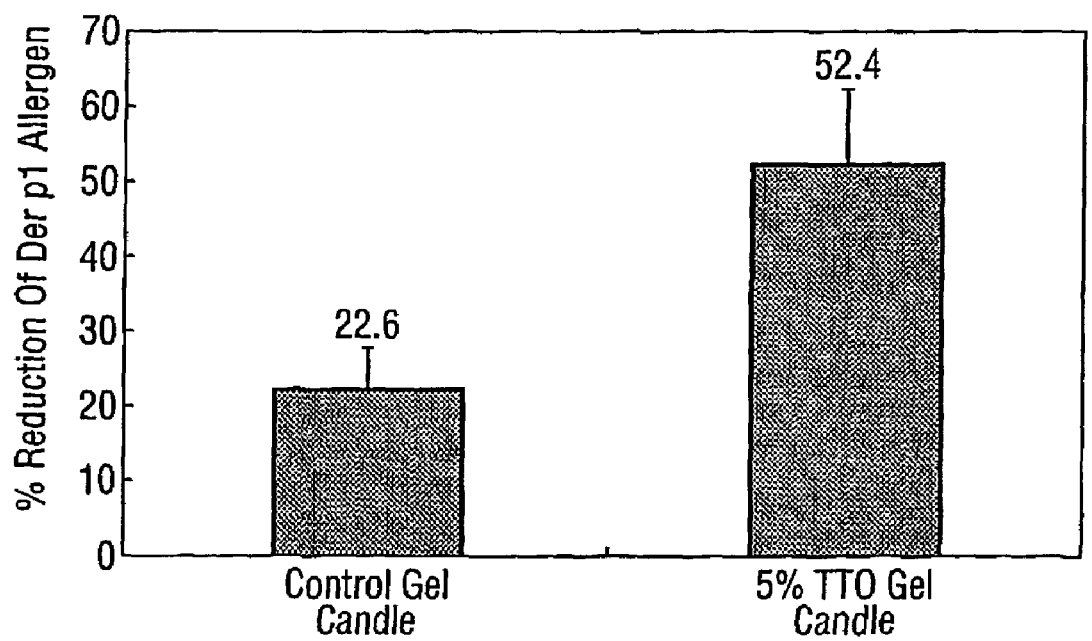

Experiments were completed using the same method as described in Example 5 except that dust samples were exposed in each booth at the same time. 0.025 g of dust was distributed evenly over a 0.32 m² aluminum tray. Half of this was then removed as a control sample as described in Example 5 and the tray was placed in the booth. Five other trays were prepared in this way and placed in the booth. The six trays containing the test dust samples were exposed in the booth to a five hour burn of the selected candle. The trays were left exposed in the booth for a further 17 hours, and the test dust samples were then collected and assayed by the appropriate ELISA. FIG. 8 show a comparison of the % Der-p1 allergen reduction after exposure to clear gel candles containing 0% (control) or 5% tea tree oil.

The reduction of allergen concentration in the dust was significant after exposure to the gel candle containing tea tree oil.

EXAMPLE 8

Experiments were completed using the same method as described in Example 4. However, instead of burning a candle, a nebulizer was used to deliver the volatile oils.

The ultra-sonic jet nebulizer used in Example 2 was used in these room tests. When the nebulizer was activated, a jet of cold, ultra-fine mist was expelled from the top of the reservoir. Tests were completed with 5 ml of either tea tree oil or Unitene® D floated on top of 150 ml deionized water in the nebulizer.

Figure 9:
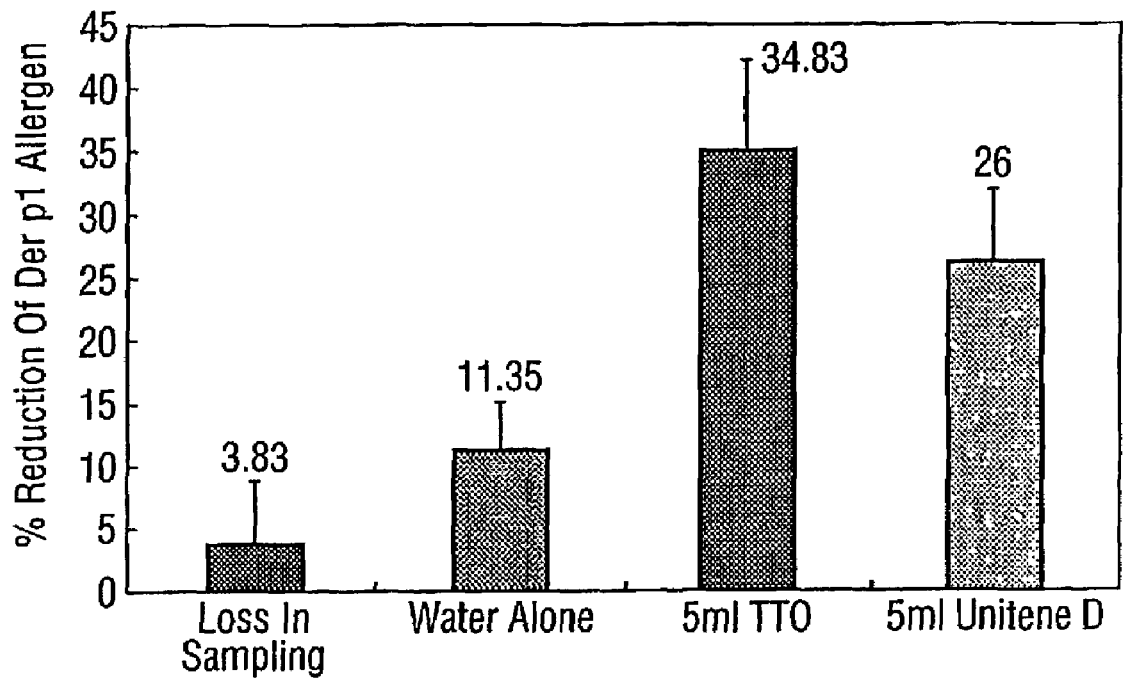

The nebulizer was activated for three hours. It is not known exactly how much of the volatile oil was released, as some of the water/oil mixture remained in the nebulizer at the end of the test. Controls were completed with deionized water alone in the nebulizer. The results are given in FIG. 9.

There was a significant reduction of the allergen content of the dust after exposure to the tea tree oil or Unitene® D.

EXAMPLE 9

Figure 10:
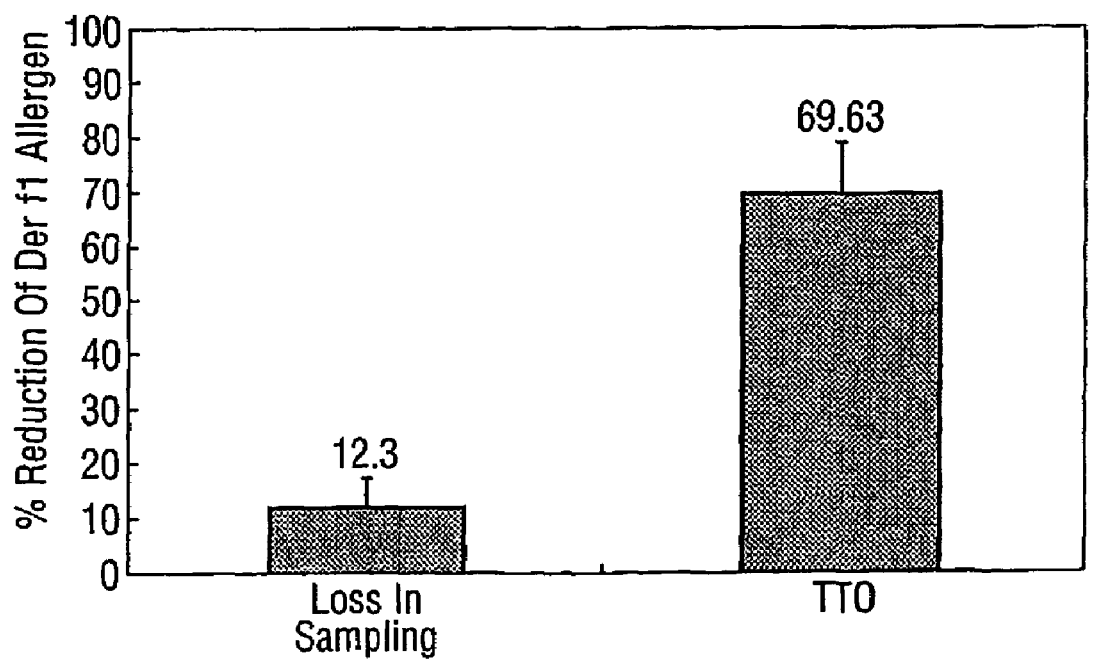

Experiments were completed as detailed in Example 1, but with American house dust. Test dust samples were exposed to oil burners in small booths containing 800 μl of tea tree oil floated on 6 ml of distilled water. These were compared dust lost in sampling. Dust samples were collected after 24 hours and assayed by Der-f1 ELISA. The results are given in FIG. 10.

There was a significant reduction of the allergen content of the dust after exposure to the tea tree oil.

EXAMPLE 10

Experiments were completed using the same method as described in Example 4. However, instead of burning a candle, oil burners were used to deliver the tea tree oil.

Two types of oil burners were used in the tests. Small oil burners were used in the small booth tests (detailed in Example 4) and in one of the test room tests. The oil burners were ceramic with a small dish with a 15 ml capacity to hold the water and volatile oil. A single tea candle was placed under the suspended dish to evaporate the water and tea tree oil. Large oil burners were used in the remaining tests completed in 28 m³ test rooms. These were also ceramic and had a large dish with a 35 ml capacity and were wider in the base so that three tea candles could be placed under the dish to evaporate this larger amount of liquid more efficiently. The tea tree oil was always floated on water in the oil burners as this regulated the temperature and enabled a controlled release rate of the tea tree oil.

Figure 11:
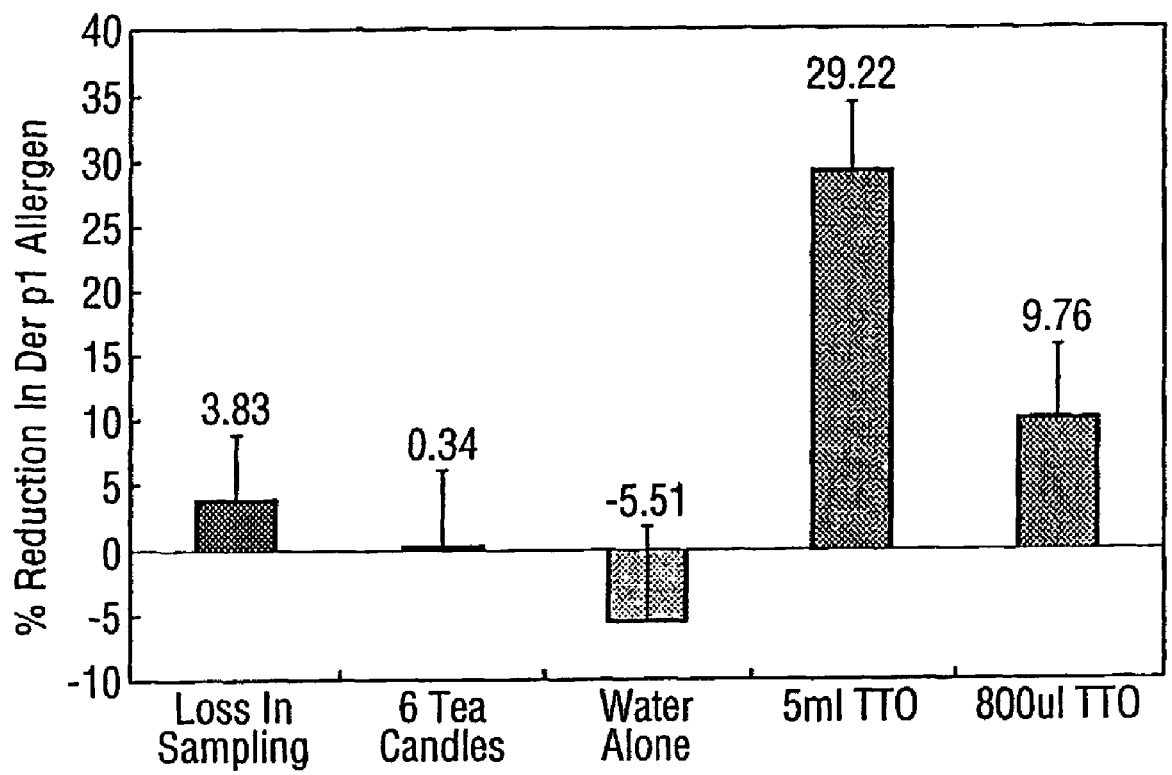

Two large oil burners were used in most of the room tests, as this was a much larger volume over which to deliver the water and tea tree oil. Two large oil burners contained in total 65 ml of deionized water and, where specified, 5 ml of the tea tree oil. This was not a direct translation of the small booth tests as it was found that this would have been unrealistic (336 ml water and 44.8 ml test chemical). They were placed in the rooms and the candles burnt until all of the liquid had evaporated. Tests were completed with tea tree oil. Controls were conducted with deionized water alone in the oil burners. To quantify any effect due to the candles, tests were conducted with six tea candles alone. One test was also completed with a small oil burner containing 6 ml of water and 800 μl of tea tree oil, so that a comparison could be made with the small booth tests. The results are given in FIG. 11.

There was a significant reduction of the allergen content of the dust after exposure to the tea tree oil.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of deactivating at least one of an airborne Der-p and an airborne Der-f allergen which method comprises vaporizing into a space containing said allergen a deactivating amount of a volatile oil comprising at least one terpene hydrocarbon, the vaporizing being done by placing the volatile oil in a reservoir into which a wick has been dipped and then lighting said wick.

2. The method according to claim 1 wherein the volatile oil is floated on water.

3. The method according to claim 1, wherein the volatile oil is provided an oil-in-water emulsion containing not more than about 5% by weight of the volatile oil.

4. A method of deactivating at least one of an airborne Der-p and an airborne Der-f allergen which method comprises vaporizing into a space containing said allergen a deactivating amount of a volatile oil comprising at least one terpene hydrocarbon, the vaporizing being done by incorporating the volatile oil into a candle and lighting said candle.

5. The method according to claim 4, wherein the candle comprises at least about 2% by weight of the volatile oil.

6. The method according to claim 5, wherein the candle comprises at least about 10% by weight of the volatile oil.

7. The method according to claim 4, wherein the candle is burnt for at least about 2 hours.

8. The method according to claims 1 or 4, wherein the oil comprising at least one terpene hydrocarbon comprises a pinol.

* * * * *